United States Patent [19]

Companion et al.

[11] Patent Number: 4,852,578

[45] Date of Patent: Aug. 1, 1989

[54] RAPIDLY QUANTIFYING THE RELATIVE DISTENTION OF A HUMAN BLADDER

[75] Inventors: John A. Companion, Hampton; Joseph S. Heyman, Williamsburg, both of Va.; Beth A. Mineo; Albert R. Cavalier, both of Arlington, Tex.; Travis N. Blalock, Knoxville, Tenn.

[73] Assignee: The United State of America as represented by the Administrator of the National Aeronautics and Space Administration, Washington, D.C.

[21] Appl. No.: 118,993

[22] Filed: Nov. 10, 1987

Related U.S. Application Data

[63] Continuation-in-part of Ser. No. 929,869, Nov. 13, 1986, abandoned.

[51] Int. Cl.$^4$ ............................................. A61B 10/00
[52] U.S. Cl. .................................................. 128/661.03
[58] Field of Search .................................... 128/661.03; 73/596-600, 602

[56] References Cited

U.S. PATENT DOCUMENTS

| | | | |
|---|---|---|---|
| 3,872,858 | 3/1975 | Hudson et al. | 128/660 |
| 4,341,120 | 7/1982 | Anderson | 128/660 X |
| 4,383,533 | 5/1983 | Bhagot et al. | 128/663 X |
| 4,564,018 | 1/1986 | Hutchison et al. | 128/660 |
| 4,662,380 | 5/1987 | Riley | 73/631 X |

OTHER PUBLICATIONS

Wells, P. N. T. "Ultrasonics in Clinical Diagnosis", Churchill Livingston, N.Y. 1977, pp. 148–151.
Mortimer, A. J. et al., "System for Histogram Production in Automatic Midline Echoenceephalography", MBEC vol. 15, 1977, 1977 pp. 78–80.
Ostro, P. et al., "Digital UTS Image Processing w/Microprocessor Manipulation".
Jrnl. of Med. Engrg. & Technology, vol. 2 #5, (Sept. 1978) pp. 234–238.
Hoshino, H. et al., "Microprogrammable UTS Image Processor", SPIE vol. 314, DIG. Radiography (1981) pp. 354–361.

*Primary Examiner*—Francis Jaworski
*Attorney, Agent, or Firm*—George F. Helfrich; John R. Manning; Charles E. B. Glenn

[57] ABSTRACT

A device and method rapidly quantifying the relative distention of the bladder of a human subject are disclosed. Ultrasonic transducer 1, which is positioned on subject 2 in proximity to bladder 16, is excited by pulser 3A under command of microprocessor 4 to launch an acoustic wave into patient 2. This wave interacts with bladder walls 12,13 and is reflected back to ultrasonic transducer 1, when it is received, amplified and processed by receiver 3B. The resulting signal is digitized by analog-to-digital converter 5 under command of microprocessor 4, and is stored in data memory 6B. The software in microprocessor 4 determines the relative distention of bladder 16 as a function of the propagated ultrasonic energy; and based on programmed scientific measurements and individual and anatomical and behavioral characteristic of with the specific subject as contained in program memory 6A, sends out a signal to turn on any or all of the audible alarm 7, the visible alarm 8, the tactile alarm 9, and the remote wireless alarm 10.

4 Claims, 6 Drawing Sheets

RAPIDLY QUANTIFYING THE RELATIVE DISTENTION OF A HUMAN BLADDER

ORIGIN OF THE INVENTION

The invention described herein was jointly made: in the performance of work under a U.S. Department of Education/National Institute for Handicapped Research grant to the Association for Retarded Citizens of the United States, and is subject to the provisions of the Education Department General Administrative Regulations, revised July 1, 1985: and in the performance of work under a NASA Contract, and is subject to the provisions of Section 305 of the National Aeronautics and Space Act of 1958, Public Law 85-568 (72 Stat. 435: 42 USC 2457).

This application is a continuation-in-part of co-pending Application Ser. No. 06/929,869, filed Nov. 13, 1986 and now abandoned.

BACKGROUND OF THE INVENTION

This invention relates generally to the rapid signature analysis characteristic of changes in an elastic membrane caused by stress, as a function of energy transmitted into the membrane and reflected therefrom. It relates particularly to a device for rapidly quantifying the relative distention of the bladder of a human subject as a function of ultrasonic energy transmitted into the subject and reflected therefrom.

There has been a long standing need for a device for rapidly quantifying the relative distention of bladders of human subjects, especially the mentally retarded, the infirm, the elderly and those with quadriplegia.

In attempts to normalize the lives of persons with mental retardation, much energy has been devoted to teaching these persons how to function independently in society. The problem of incontinence often thwarts the best of these efforts while sophisticated toilet training programs are quite successful in teaching some persons what to do once the internal sensation of a full bladder is perceived, these programs typically presuppose that a person is capable of realizing when she/he has to void. The subset of the population of persons with mental retardation for whom continued incontinence is a more common problem are those persons with severe or profound mental retardation, i.e., those with IQs less than 35 and significant deficits in adaptive behavior, who have difficulty in recognizing the subtle and somewhat obscure signals of their bladders.

In addition, there is a substantial need to provide increased independence for persons who have permanently lost the ability to control their bladders for medical reasons such as diabetes, cerebral palsy, quadriplegia, spina bifida, and advanced age.

Incontinence typically results in a stigma for the person, reduced positive interaction with other people, unsanitary living conditions, excessive laundry expenses, and increased custodial attention by caregivers. Because of the failure to acquire fundamental toileting skills, such persons are often excluded from a wide variety of vocational, social, and recreational programs, in addition to many preschool programs—all of which are important components of overall experience necessary for their developmental growth and eventual integration into community life.

Previous attempts to employ technology in urinary toilet training fall into two classes. The first class is the wetness detector, which alerts the subject when urine is present on the person. A particular example of this is the employment of a moisture-sensitive apparatus in the clothing or in the bed, which device triggers an alarm when moisture is detected. The second class is the motion-sensitive device, which is located in the toilet. Once/voiding has begun, the motion imparted to this device triggers an alarm which helps the user recognize that urination has been initiated. However, both classes of devices produce their effects after urination has taken place. That is to say, their users are helped to recognize when voiding has been initiated, but they are not helped to recognize the preliminary need to urinate, and thereby make the association between this need and socially-acceptable toileting behavior. In neither case is there a quantification of the relative distention of the bladder, which would be of significance in helping one to recognize the preliminary need to urinate.

Urologists have recently employed an ultrasonic device which scans the entire bladder and images it with a sector scan to show the extent of the bladder wall over a sixty degree angle. Other recently-developed devices are based on an ultrasonic "A" scan technique, using the time of flight of the sound wave between the front and back walls. These devices are typically bulky and expensive. Moreover, even the most sophisticated of the current devices suffers from inaccuracies resulting from the assumption of a simple, usually spherical, shape for the bladder. In actuality, the bladder is not a sphere, rectangle, or other simple geometric shape. It varies in shape continuously as it fills, varies in shape as between individuals, varies in height relative to the pelvic girdle as between the sexes, and if it ever did approach the point of becoming a sphere, hyperdistention would be imminent.

While 50 cc of urine is considered to be a significant void volume, void volumes in test subjects varied from 30 cc up to over 1000 cc. The test population to date has tended to void between 180 and 400 cc. The subject's perception is of increasing discomfort above approximately 200 cc. In individuals with urinary disfunction the bladder has been inflated through a catheter to upward of 600 cc with no real sensation being reported.

It is therefore a primary object of this invention to provide a device for the quantification of the relative distention of the urinary bladder of a human subject over a wide range of volumes, and with greater accuracy than any non-scanning ultrasound device available from the prior art.

A further object of this invention is to provide adaptability to the requirements of a human subject in a user selectable manner, thereby mimicking normal perception and affording help to the subject in recognizing the appropriate tide to urinate. Since an intended application of the present invention is for individuals experiencing bladder dysfunction for varying reasons and at varying ages, an adaptable operating system is a must. A microprocessor based design, with as much as possible of the functionality of the device in software, is indicated.

A further object of this invention is to provide a device for rapidly quantifying the relative distention of the bladder of a human subject, thereby providing vital information needed by the subject during the critical time when the bladder is at or near its full extension, and affording help to the subject in recognizing the preliminary need to urinate.

Other objects and advantages of this invention will become apparent in the specification and drawings which follow.

SUMMARY OF THE INVENTION

The present invention comprehends the provision of an ultrasonic transducer, which is positioned in proximity to the abdomen of the subject under test, for the purpose of transmitting energy in the form of acoustic waves into the bladder of the subject followed by receiving acoustic waves reflected from the bladder of the subject. A pulser/receiver communicates with a source of power and the transducer and excites the transducer to transmit energy in the form of acoustic waves. It also amplifies and processes the reflected acoustic waves received by the transducer and provides analog signals representative of at least one reflected ultrasonic waveform over a respective time interval. A converter communicates with the pulser/receiver to digitize the analog signal from the pulser/receiver to provide a corresponding digital signal representative of at least one waveform. A memory communicates with the converter for storage of the digital signal from the converter. An input means provides a digital input signal representative of a characteristic of the subject related to the amount of urine in the bladder. A logic system communicates with the pulser/receiver to command excitation of the ultrasonic transducer. The logic system communicates additionally with the converter to command digitization of the analog signals from the pulser/receiver. The logic system also communicates with the memory to receive the digital input and the stored signals for processing the stored signals to provide a function signal related to the value of the digitized signals and their time of occurrence within the respective time intervals, and for comparing the function signal with stored, preselected function levels to determine equivalency and to activate a preselected alarm upon the attainment of equivalency. The relative distention of the bladder of the human subject is thereby rapidly quantified.

According to the present invention, an ultrasonic transducer is placed in contact with the skin of the subject on the midline, just above the pubic symphysis. The transducer is coupled to the skin by means of a medically approved, water-based couplant. The transducer serves as both pulser and receiving element in the pulse-echo system. An analog to digital converter processes the amplified echo return and supplies eight bit amplitude data, in a histogram format, to a controlling microprocessor. All control functions are contained in EPROM or are selectable from front panel BCD switches.

The genesis of this device was the need for an inconspicuously small, battery operated monitor that could be worn by an individual during the course of normal activities. The device should be adjustable by the individual in areas such as setting the appropriate volume level for the alarm to be given, and the type, intensity, and duration of the alarm. Further, variations of the programming should be selectable, including a setup mode to assist in proper positioning of the transducer, as well as slightly different versions of the program to optimize the signal processing for individuals of different body sizes and configurations.

In the interests of mechanical, electrical and fiscal simplicity, an "A" scan format was chosen. The signal processing differs from the prior art as used in other "A" scan based instruments, which, even were they to be reduced to a comparable size, would suffer from inaccuracies in the interpretation of the "A" line scan, related to the non-symmetric mode of expansion of a real bladder.

From *Grey's Anatomy* the depiction of the bladder shows an organ that is well above the pelvic basin and with the major axis roughly parallel to the abdominal surface in infancy. As the individual ages, the bladder sinks toward the pelvis. In the female, probably beginning at puberty, the bladder is typically lower than in the male. As the bladder slides down and back over time into the pelvis, the major axis becomes more horizontal. In both the transverse and sagittal sections the bladder is roughly triangular, until some degree of distention is arrived at. The progress of fill of the bladder is as follows: the cavity of the empty bladder takes the shape of a flattened "Y", with the urethra at the bottom. This is true in both the fore-aft plane and the lateral plane. The "Y" gradually fills to the top and then the actual expansion begins. The bladder expands in the fore-aft plane, and in the vertical plane, giving rationale for the front-wall to back-wall time of flight measurements. However, as will be delineated hereinafter, the non-symmetric expansion of the bladder limits both the dynamic range and the overall accuracy of a strictly time-based system.

In the information content of any ultrasound scan into the abdomen, there are a number of givens: the transmitted pulse and its associated decay will be present, the transducer-skin interface will produce an echo, the skin to underlying muscle will produce an echo, and the muscle to abdominal cavity interface will produce an echo. These echoes will always be present in the early portion of the return, on all subjects. At low levels of inflation, the front wall of the bladder is a poor target. It is a rounded point in the transverse section and even more acute in the sagittal section. There is no single true diameter. To compound the problem, as the bladder expands, while it does become a better target, the front wall also moves toward and eventually merges with the ever present abdominal wall echoes at the front of the returning echo. All of this makes the front wall, for much of the range of bladder expansion, a poor marker. All of this does not negate the value of time of flight measurements, however, as the back wall will remain in view, and the transducer itself can serve as the first marker.

The time of flight measurement, however, has an additional deficiency— lack of dynamic range. If the bladder were expanding in a vacuum, this would not be the case. In the body, however, the bladder soon runs out of room to expand to the rear, the sides and the front. Taking the path of least resistance, the primary direction of expansion in the upper ranges of volume is vertical, lifting and displacing the intestines. Movement in individuals who have had major abdominal surgery can produce some interesting vectors.

An additional factor that has a bearing on the analysis of data derived from an "A" line scan is that the movement of the back wall of the bladder, other than in very young children, is not a direct translation, but rather the elevation of the angle of a curved surface relative to the axis of the insonating beam. Further, as this surface becomes more perpendicular to the axis, it is also effacing the rugose folds characteristic of the lining of the empty bladder. The net effect of these actions is to make the back wall a better reflector as the bladder distends.

There are two other mechanisms having an effect on the echo return at higher volume levels which have now come to light as a result of the present invention. At any acoustic interface, some portion of the incident wave will be reflected and some will pass through. This is true of the back wall of the bladder, particularly at the higher levels of distention. The insonating beam passes through a greater distance of the low attenuation urine than formerly, and the back wall has become a better target. Some portion of the energy will penetrate the back wall and produce reflections from the muscle layers surrounding the bladder. In addition, the distended bladder is now pressing against the organs and blood vessels that surround it.

Movements and pulsations in these organs are impressed on the wall of the bladder. The net effect of these two conditions is to cause an apparent increase in the duration of the back wall echo, which is related to increasing distention.

The difference between the present invention and previous "A" scan technology is that the resident software algorithm keeps track of all of the variables, assigns weighted values to them, depending on their relative information content, and then derives a discrete numerical value for the perceived volume in each scan. That value is put into memory and the trend of the value is periodically time averaged, with that resultant both saved and made available for display.

By fully exploiting not just the location of the bladder wall, but also the information extractable from the changing signature of the wall echoes, the range of volumes through which the relative bladder distention can be tracked is substantially enhanced.

As is understood by those of skill in the art from the foregoing, rapid quantification of the relative distention of the bladder of a human subject is achieved according to the present invention by transmitting an acoustic wave into the bladder of the human subject so as to create a reflected acoustic waveform: measuring a time range together with an energy level of the reflected acoustic waveform: applying a signal processing algorithm thereto; and comparing the resulting measurement against a selectable standard.

BRIEF DESCRIPTION OF THE DRAWINGS

For a more complete understanding of the present invention, including its objects and benefits, reference should be made to the detailed description, which is set forth below. This detailed description should be read together with the accompanying drawings, wherein.

DETAILED DESCRIPTION OF THE INVENTION

Figure 1:
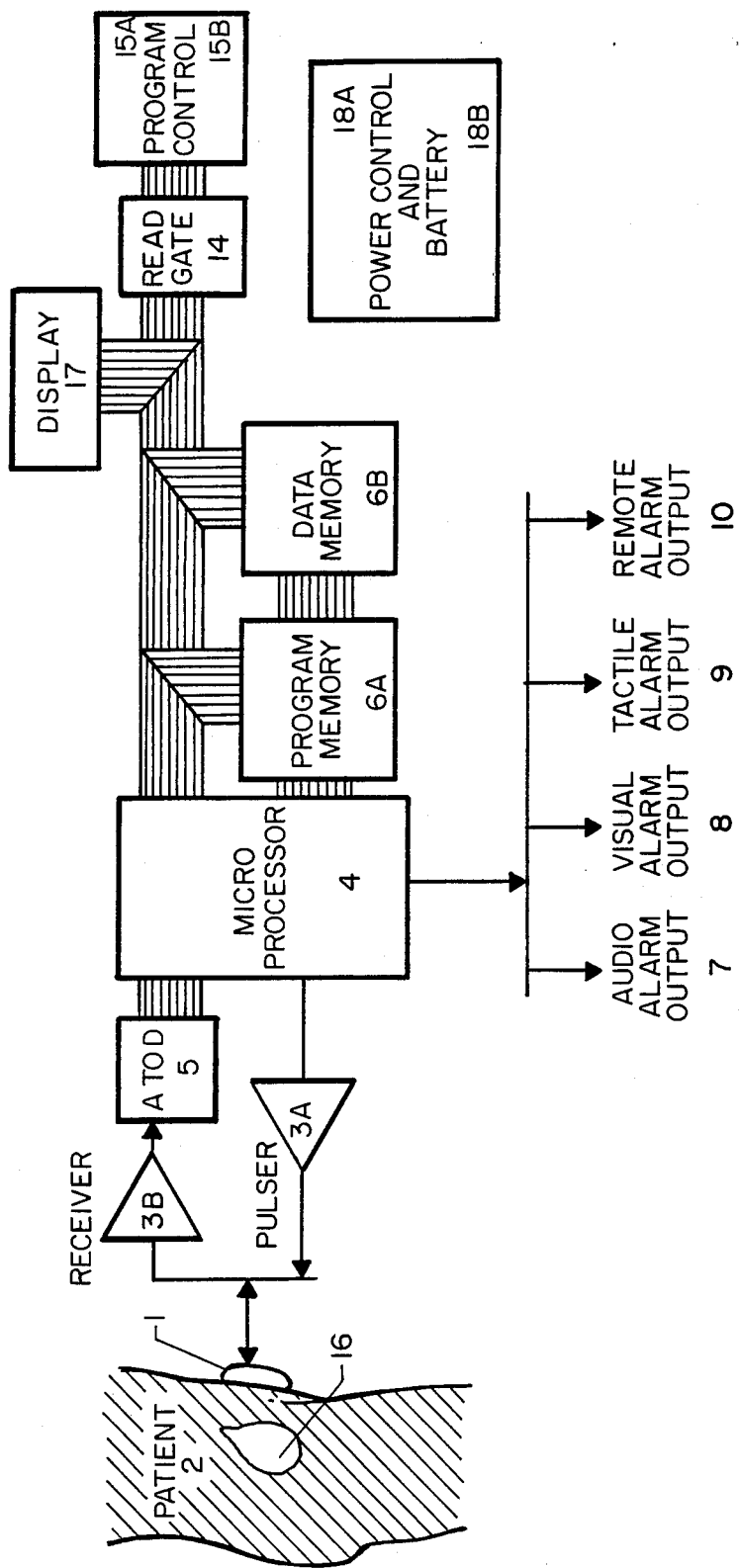
FIG. 1 is a functional block diagram of a preferred embodiment of the present invention, FIGS. 2(a), (b), (c) is a three-part diagram showing in simplified graphic form the acoustic beam path interaction with an empty bladder: a rendering of the oscilloscope presentation of the amplified and detected output resulting from that interaction; and the same waveform in digitized format, respectively.

The block diagram in FIG. 1 illustrates a preferred embodiment of the device according to the present invention. The system is under the control of microprocessor 4, with all programming stored in a 64K EPROM 6A,B. At turn on, read gate 14 is enabled and the status of the two BCD switches 15A,B is determined. Switch 15A sets the desired volume level at which an alarm is to be sounded. Switch 15B selects the operating mode of the system and the display status. The microprocessor 4 then sends the first command to pulse. This pulse activates power amplifier 3A which drives transducer element 1. The piezoelectric transducer element produces a burst of 0.5 MHz sound waves when the 300 nano-second, 12-volt DC pulse is applied to it. This is the transmit portion of the scan, which lasts for approximately 40-microseconds including the pulse decay time. The system then goes into a listening mode for approximately 250-microseconds. The receiver 3B consists of an input differential amplifier; and absolute value detector, and an output gain block. The output of the receiver is limited to a swing between 0 and ±5 volts. Any returning echo is amplified, conditioned, and applied to the input of analog-to-digital converter 5. The converter is enabled by the same command to pulse as the power amplifier. Since the receiver "sees" the transmitted pulse as well as the echo, the first 40-microseconds after $T_O$ is ignored. This prevents the transmitted pulse from creating an error artifact. Starting after the end of the transmit pulse, the A-D converter 5 performs 128 successive quantizations, each occupying a time block of 1.7 microsecond. The depth into the abdomen of patient 2 insonated in this length of time has proven, in all of the test cases to date, to be sufficient to view the back wall of bladder 16.

The echo return contains some amount of low level noise, which can be removed by thresholding. Short term pulsations (usual duration approximately ½ second) that appear to be caused by peristaltic action in the intestines, are removed by time averaging. Because the amount of intestinal overlay of the bladder and the resident ambient noise is quite variable between individuals—with children so far tending to give cleaner returns than adults—the number of scans to be averaged, their spacing and the update rate can all be varied to suit the user. Between active cycles, power control 18A is employed to maximize the life of battery 18B. In the current configuration (which was optimized for a test population of adult males) four individual pulse-echo scans are taken and processed at eight millisecond intervals, the results are averaged, the weighting algorithm is performed, and the results thereof placed into data memory 6B. Four seconds later another group of four scans is taken, processed, averaged and placed into data memory 6B. This procedure is repeated four times. After the fourth iteration, the results of the entire group are averaged, the output of display 17 is updated, and the numerical value is compared to the value of the desired alarm volume level. If the currently perceived volume value meets or exceeds the desired level, then the selected alarm alarms are activated. In order to accommodate the varying needs of the individual users, both the type and the duration of the alarm are switch selectable. The alarm suite is comprised of visual 8, tactile 9, and audio 7 (volume is also adjustable), and remote 10. Alarm duration is adjustable from one second to eight seconds in one second increments.

In actual practice, the setup and utilization of the device of the present invention is straightforward. The individual under test is allowed to accumulate some quantity of urine in the bladder by simply drinking a fluid and waiting approximately thirty minutes. The transducer 1 with a suitable couplant is applied to the abdomen of subject 2 in the area just above the pubic hair. The transducer 1 is then moved around to obtain a maximum reading on display 17 with the device set to pulse continuously. This is taken to be an indication that bladder 16 is in the view of the insonating beam, as an empty bladder or a misaligned beam will afford very low numerical values. The (arbitrary) numerical range shown on display 17 has typically varied in the test population from a value of 8–10—representing an essentially empty bladder—up to a reading of 55–65—representing volumes in excess of 500 cc. Alarm level switch 15A permits the selection of sixteen levels ranging from 9–57. This is an arbitrary range based on the statistics of the test population who tended to void between values of twenty-four, which typically gave volumes of 240–260 cc, and forty-two, which gave volumes of approximately 400 cc. The transducer 1 is secured to patient 2 by an elastic belt, similar in construction to a hernia truss belt. The electronics package, including power control 18A and battery 18B, is carried in a case on a shoulder strap.

In practice, with the device being worn by an individual for an extended period of time who is going through the normal daily routines, some operational characteristics were noted. When a normal, functioning individual accumulates some volume in his/her bladder, the physiological sensation is not constant. When the feeling of need to urinate is first apparent, it comes and goes, and the individual can be distracted. As the volume of urine increases, however, so does the frequency and urgency of the sensations, until such point as the individual feels substantial discomfort, which may be distracting from the task at hand, and he/she decides to void. Throughout, there are strains and postures that increase the physiological sensations. These are, however, transitory until the volume of urine becomes excessive.

The present invention mimics the type of progression set forth above. Since it is reasonable to assume that the individual will want to accumulate an appreciable volume of urine in the bladder before taking the time to void, an intermediate alarm level was selected for the test program. It was noted that when the bladder is empty, or when it has a very small amount of urine therein, body movement did not produce any false alarms. When some amount of urine (80–100C) is present in the bladder, however, then body movement can produce an occasional, transitory alarm. When such movement ceases, the alarm stops. Of course, the individual could choose to void at this time, but, as is usually the case with normal perception, the individual does not choose to void at the first sensation. Rather, as time goes on and the alarm trigger level is approached, the alarm (again as with the natural sensation) becomes more and more frequent, until they are annoying. The individual, or the individual's caretaker can over a period of time adjust the alarm level to that point which works best for the individual involved eliminating false positives for certain individual.

Figure 2A:
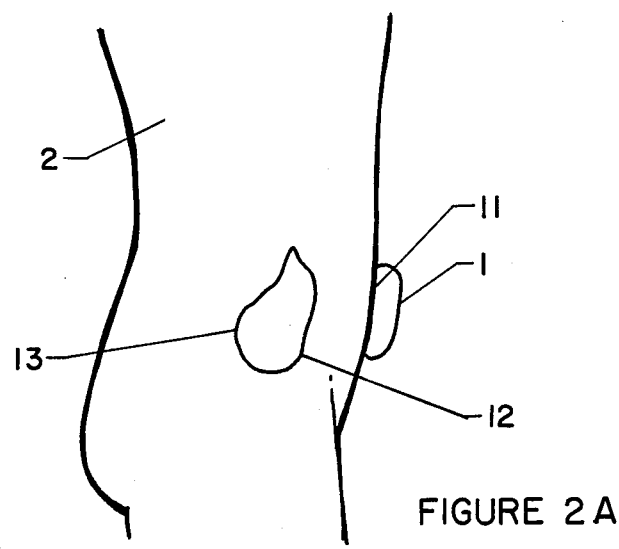
Figure 2B:
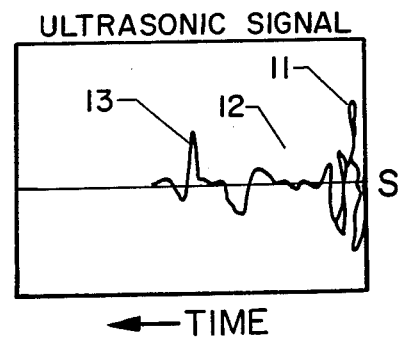
Figure 2C:
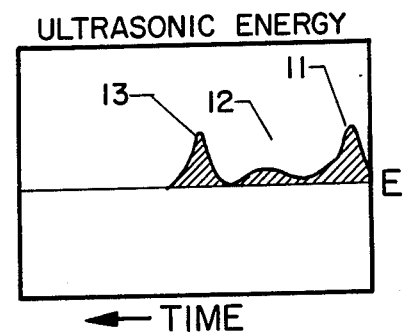
Figure 3A:
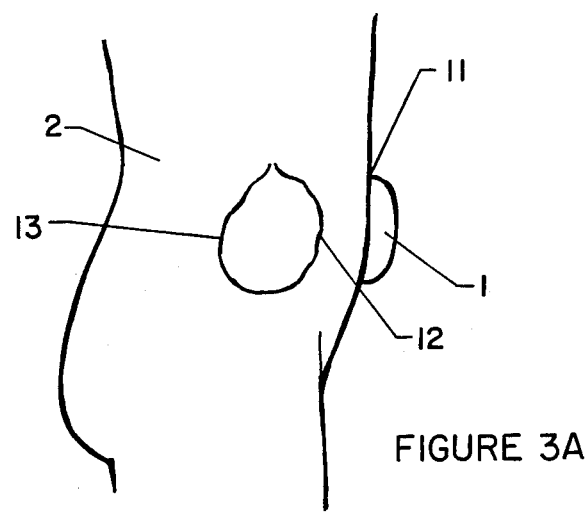
FIGS. 3(a), (b), (c) is a three-part diagram in the same format as FIG. 2, but with the bladder in a partially distended state.
Figure 3B:
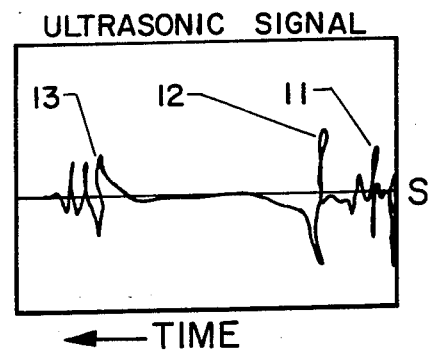
Figure 3C:
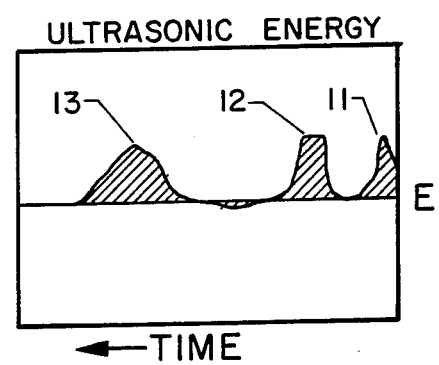
Figure 4A:
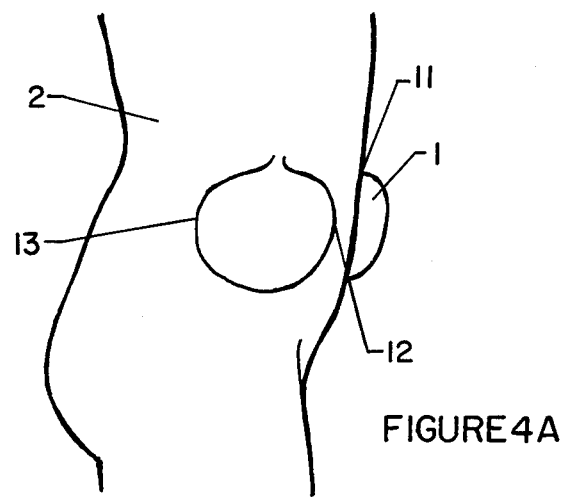
FIGS. 4(a), (b), (c) is a three-part diagram in the same format as FIGS. 2 and 3, but with the bladder in a well-distended state.
Figure 4B:
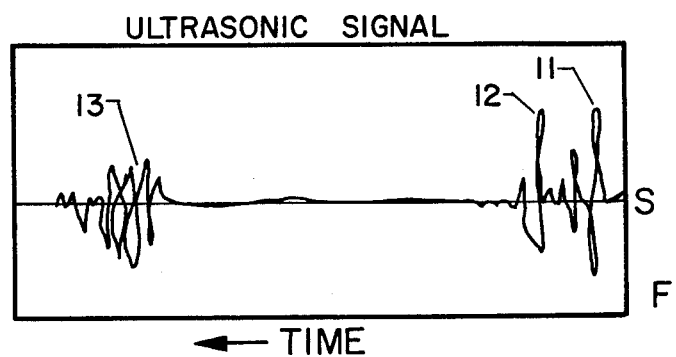
Figure 4C:
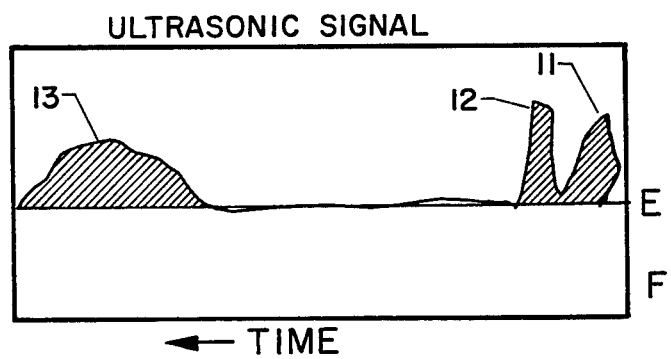

To better understand the function and operation of the invention, it is necessary to examine the acoustic wave interaction with the bladder as is shown in FIGS. 2–4. In FIGS. 2(a–c), the bladder is essentially empty. In FIGS. 3(a–c), the bladder is being filled, and in FIGS. 4(a–c) the bladder is at maximum fullness. In each of FIGS. 2–4 are simplified, illustrative diagrams of the physical bladder and the ultrasonic transducer (A), a conventional ultrasonic signal S showing the electrical radio frequency (RF) wave forms obtained from the transducer after conversion in the receiver(B), and the energy wave forms E (C). Each of FIGS. 2–4 shows the tissue/transducer interface 11, the bladder front wall 12, and the bladder rear wall 13.

In FIG. 2, with the bladder essentially empty, transducer 1 is placed on the patient with a conventional couplant for ultrasound. The sound wave excited by the pulser/receiver 3 of FIG. 1 causes the ultrasonic signal shown in FIG. 2, diagram 2B, time position 11. The wave also reflects off the bladder front wall 12 and the bladder rear wall 13, with the resulting ultrasonic signals 12 and 13, respectively, in diagram 2B. The bottom diagram 2C in FIG. 2 is the ultrasonic energy with its corresponding signals 11, 12, and 13. These signals are obtained by adding the absolute amplitude of the RF wave forms for each pulse and averaging the resulting summation over N cycles of the measurement, in accord with the value weighting function by the programmed algorithm.

In FIG. 3, with the bladder partially full, the bladder has inflated as shown in diagram 3A of the figure, and the RF waveforms have changed as the bladder shape has changed. In particular, the rear wall reflection has moved back in time, and additional reverberation has built up in the rear wall signal as shown in 3B, wave 3 as well as in 3C, wave 3.

In FIG. 4, with the bladder substantially full, the change in shape has continued, although the rear wall 13 has not moved in a simple fashion during filling. The energy seen in the rear wall reflection, however, continued to increase as the bladder was being filled. In fact, for a bladder filling past about 60% fullness, the rear wall hardly moves at all, while the energy reverberation at the rear wall continues to increase. Thus, it can be seen that a monitor of the rear wall position only would not be accurate during critical near-full periods. In sharp contrast thereto, this invention, which measures the energy in the rear wall reflection as well as the rear wall position, is accurate as a monitor for the entire range of bladder fullness.

Figure 5A:
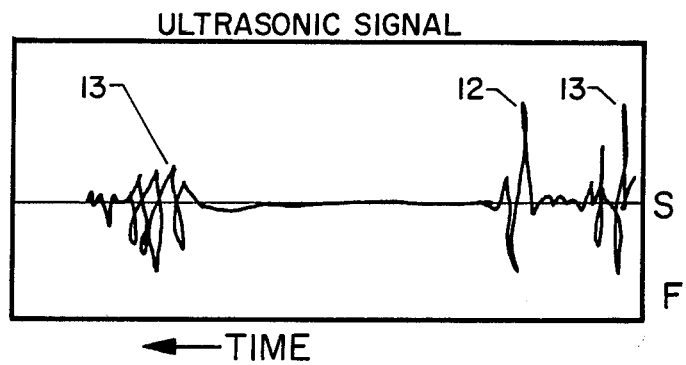
FIG. 5(a) is an amplitude histogram of a discrete digitized echo waveform.
Figure 5B:
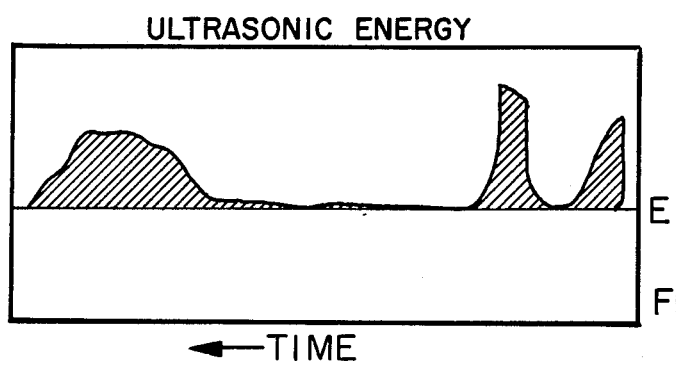
FIG. 5(b) is a graphical illustration of a time/weighting curve applied to the date in FIG. 5(a)
Figure 5C:
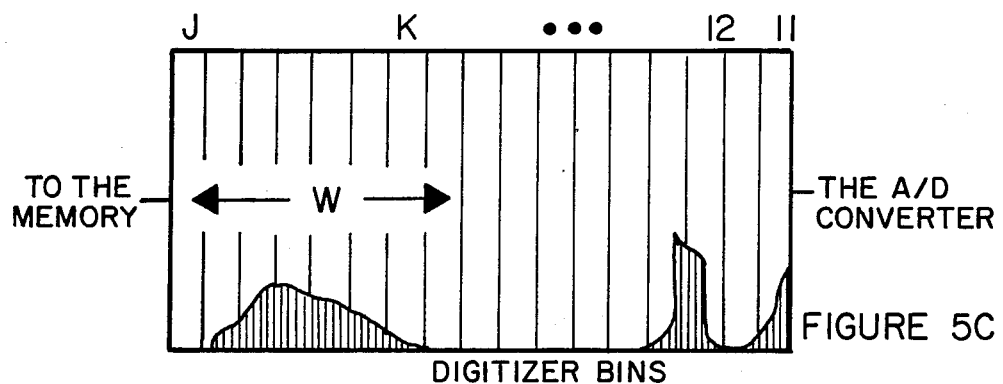
FIG. 5(c) is the resulting weighted histogram which will be processed by an algorithm to give a numerical equivalent.
Figure 6:
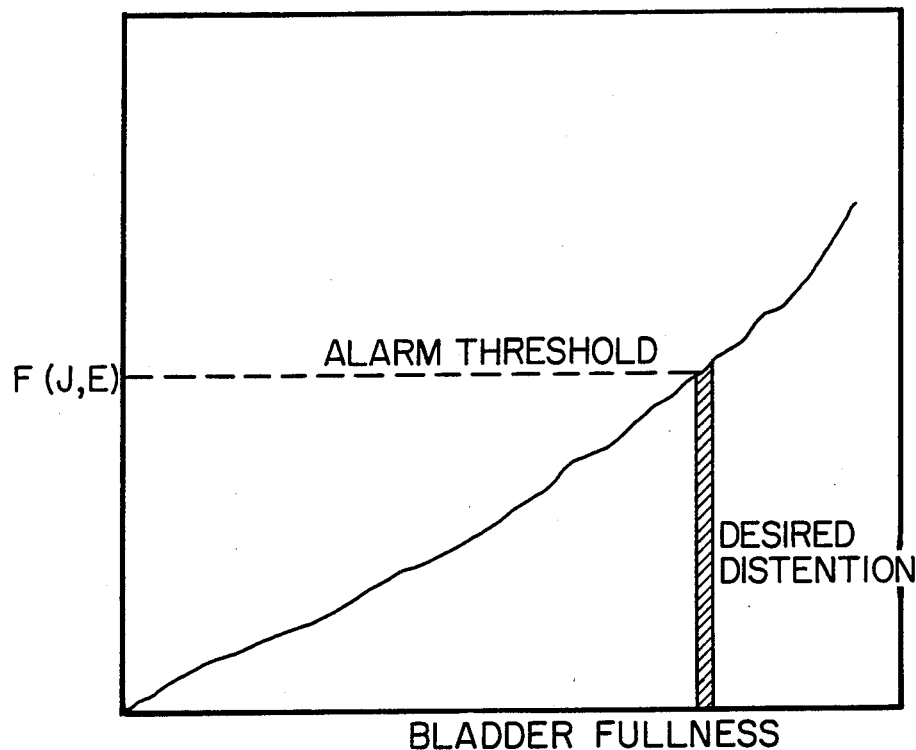
FIG. 6 shows the progression of a typical data trend line versus desired volume for alarm activation.

FIGS. 5 and 6 relate to the internal components of this invention and their function in more detail. The converter 5 and the memory 6 actually act as a signal averager, taking the digitizer output and multiplying it by some weighting function related to bin number, while checking that the signal falls in the correct time range or bin number (J). The entire operation is controlled by the software to configure the function and the mathematical operations for the specific subject.

As the simplest case, the function used is the sum of energy amplitudes in bins $(J-K\pm W)$ that correspond to the rear wall and beyond of the bladder, where W is the width of the reverberation signal at the rear wall. A check on the data quality is that bins less than $(J-K)$ show no significant amplitude. Such a lack of signal corresponds to the fact that when the bladder contains water, the path length between the front and rear walls should show no scattering, i.e., a simple water path exists.

The internal logic calculation of FIG. 6 shows the result of a typical bladder during filling. The function has been adapted to the specific subject so that the F(J,E) and the alarm threshold correspond to the best time for that subject to be notified to urinate.

A complete electronics package is worn by the subject with the transducer positioned by means of a flexible mounting belt. The electronics package advantageously contains means to alert the subject with any or any combination of a variety of stimuli including a tactile alarm (e.g., a vibrator), a visual alarm (e.g., an LED mounted on eyeglasses), an audible alarm (e.g., a buzzer), and a remote alarm (an RF link to a receiver monitor). In addition, the electronics package advantageously contains a working mode which lets the package work in a "sleep" configuration when the bladder should be empty (after successful elimination). In that mode, the frequency of pulses and measurements is reduced to lengthen the life of the power supply (which is advantageously a battery) in the package. Moreover, parameters governing the user's interaction with the device, such as typical void volume and alarm preference, are entered by the user or his/her caregiver into the logic system externally by adjusting controls on the face of the microprocessor. This affords a customization for each individual and a quick and simple modification of existing parameters at any time. The user or his/her caretaker is accordingly allowed to select the level of bladder fullness at which he/she would like the alarm to sound.

As is understood by those of skill in the art, the ultrasonic transducer, pulser/receiver, analog-to-digital converter, program and data memory, audible alarm, visual alarm, tactile alarm, and remote alarm employed herein are per se well-known, and therefore are not disclosed in detail herein.

The preferred embodiment of the invention disclosed hereinabove relates to the propagation of ultrasonic energy and averaging the energy signals over a number of measurement cycles to rapidly quantify the relative distention of the bladder of a human subject. Moreover, the programming of specific functions of the particular subject into the logic system permits a fine tuning which affords accurate operation with a wide variety of subjects and conditions.

What is claimed as new and desired to be secured by Letters Patent of the United States is:

1. A device for rapidly quantifying the relative distention of the bladder of a human subject, which device comprises:

ultrasonic transducer means for positioning on the external abdomen of the subject in proximity to the bladder, for the purpose of launching acoustic waves into the subject followed by receiving reflected acoustic waves from the subject:

pulser/receiver means communicating with a source of power and the ultrasonic transducer means for exciting the ultrasonic transducer means to launch the acoustic waves and for amplifying and processing the reflected waves received by the ultrasonic transducer means, and for providing analog signals representative of at least one reflected ultrasonic waveform over a respective time interval;

converter means communicating with the pulser/receiver means for digitizing the analog signal from the pulser/receiver means to provide a corresponding digital signal representative of said at least one waveform:

memory means communicating with the converter means for storage of the digital signal therefrom;

input means for providing a digital input signal representative of a characteristic of said subject related to the relative distention of the bladder: and logic means communicating with the pulser/receiver means for commanding excitation of the ultrasonic transducer means the logic means communicating additionally with the converter means for commanding the digitization of the analog signals from the pulser/receiver means; the logic means communicating additionally with the memory means for receiving said digital input and said stored signals for processing said stored signals to provide a function signal related to the value of the digitized signals and their time of occurrence within said respective time intervals, and for comparing said function signal with said digital input signal; thereby quantifying the relative distention of the bladder of the human subject as a function of the propagated ultrasonic energy.

2. The device of claim 1, which additionally comprises alarm means communicating with the logic system to alert the subject when the relative distention of the bladder has reached a given level.

3. The device of claim 2, wherein the alarm means is adapted to be placed on or in proximity to the subject and is selected from the group consisting of audible alarm means, visual alarm means, and tactile alarm means.

4. The device of claim 2, wherein the alarm means is adapted to be employed remotely from the subject and is selected from the group consisting of audible alarm means, visual alarm means, and tactile alarm means.

* * * * *